(12) United States Patent
Tani et al.

(10) Patent No.: US 9,131,985 B2
(45) Date of Patent: Sep. 15, 2015

(54) MEDICAL TREATMENT DEVICE

(75) Inventors: Tohru Tani, Otsu (JP); Yoshimasa Kurumi, Otsu (JP); Shigeyuki Naka, Otsu (JP); Mamoru Takashina, Asaka (JP); Hideki Ishikawa, Asaka (JP); Teruaki Oikawa, Asaka (JP)

(73) Assignee: Micron Shiga, Inc., Otsu-shi, Shiga (JP)

( * ) Notice: Subject to any disclaimer, the term of this patent is extended or adjusted under 35 U.S.C. 154(b) by 783 days.

(21) Appl. No.: 13/260,563

(22) PCT Filed: Mar. 26, 2010

(86) PCT No.: PCT/JP2010/002192
§ 371 (c)(1),
(2), (4) Date: Nov. 8, 2011

(87) PCT Pub. No.: WO2010/109908
PCT Pub. Date: Sep. 30, 2010

(65) Prior Publication Data
US 2012/0123409 A1    May 17, 2012

(30) Foreign Application Priority Data

Mar. 27, 2009    (JP) ................... 2009-080439

(51) Int. Cl.
*A61B 18/14* (2006.01)
*A61B 18/18* (2006.01)
*A61B 18/00* (2006.01)

(52) U.S. Cl.
CPC ......... *A61B 18/1815* (2013.01); *A61B 18/1445* (2013.01); *A61B 2018/00607* (2013.01)

(58) Field of Classification Search
USPC .................................... 606/20–52
See application file for complete search history.

(56) References Cited

U.S. PATENT DOCUMENTS

| 5,620,415 A | 4/1997 | Lucey et al. |
| 6,280,441 B1 * | 8/2001 | Ryan ............... 606/45 |

(Continued)

FOREIGN PATENT DOCUMENTS

| JP | 6-269460 | 9/1994 |
| JP | 2007-38003 | 2/2007 |
| JP | 2007-282666 | 11/2007 |

*Primary Examiner* — Brian T Gedeon
(74) *Attorney, Agent, or Firm* — Don D. Cha; Hamilton DeSanctis & Cha, LLP

(57) ABSTRACT

Provided is a medical treatment device capable of eliminating inconvenience of manipulation in actual clinical use, and ensuring a visual field by introducing a curve in the vicinity of an electrode portion of an outer cylindrical tube. The medical treatment device has the following structure: an electrode portion including a first electrode and a second electrode arranged opposed to the first electrode, the electrode portion having a grasping function, a coagulating function, and a cutting function; an operation portion for executing drive of the respective functions of the first electrode and the second electrode; a shaft portion for connecting the electrode portion and the operation portion; a connector portion connectable to a microwave power source; and a conductive rod, which is provided inside the shaft portion, for transmitting a microwave to the electrode portion, the medical treatment device utilizing the microwave being configured to: hold body tissue between the first electrode and the second electrode; coagulate the body tissue by supplying the microwave to the first electrode and the second electrode; and cut the body tissue through a mutual action of the first electrode and the second electrode, in which the shaft portion and the electrode portion are connected to each other with a bent holder.

10 Claims, 13 Drawing Sheets

(56) References Cited

U.S. PATENT DOCUMENTS

| | | | |
|---|---|---|---|
| 7,004,939 B2* | 2/2006 | Mackay | 606/40 |
| 7,270,664 B2* | 9/2007 | Johnson et al. | 606/51 |
| 7,678,117 B2* | 3/2010 | Hinman et al. | 606/108 |
| 8,202,288 B2* | 6/2012 | Adams et al. | 606/170 |
| 8,257,349 B2* | 9/2012 | Orszulak | 606/34 |
| 8,277,375 B2* | 10/2012 | Danitz et al. | 600/142 |
| 8,465,475 B2* | 6/2013 | Isbell, Jr. | 606/1 |
| 8,469,957 B2* | 6/2013 | Roy | 606/51 |
| 8,679,115 B2* | 3/2014 | Reschke | 606/52 |
| 2005/0234338 A1 | 10/2005 | Masuda | |
| 2007/0027468 A1 | 2/2007 | Wales et al. | |
| 2007/0173811 A1* | 7/2007 | Couture et al. | 606/39 |
| 2010/0023001 A1* | 1/2010 | Hosaka et al. | 606/33 |
| 2011/0028991 A1* | 2/2011 | Ikeda et al. | 606/130 |

* cited by examiner (A)

(B)

(A)

(A)

(B)

(C)

(A)

(B)

(A)  (B)

MEDICAL TREATMENT DEVICE

TECHNICAL FIELD

The present invention relates to a medical treatment device for holding body tissue and further coagulating and cutting the body tissue.

BACKGROUND ART

As a surgical treatment device, there is known a device in which, by utilizing microwaves, coagulation, hemostasis, incision, and the like are performed with respect to body parts such as the digestive organ, the liver, the bladder, the prostate gland, the uterus, the vessel, and the intestinal canal.

In a conventional electrosurgical knife or the like, the surface of the body tissue is heated and coagulated with the Joule heat generated using a high-frequency voltage having a main frequency of 500 kHz. In the coagulation with the Joule heat performed by the conventional electrosurgical knife or the like, the body tissue is rapidly coagulated, and hence the coagulated surface may be peeled off and dropped from the body tissue.

On the other hand, in the coagulation and the hemostasis utilizing the microwaves, the body tissue is grasped between electrodes, and the microwaves are applied to the body tissue. When the microwaves are applied to the body tissue, dielectric heat is generated, which is caused by the near electromagnetic field generated by the microwave electric power. The body tissue can be coagulated by evaporating moisture from the body tissue by the dielectric heat.

In the case of the coagulation and the hemostasis utilizing the microwaves, the body tissue can be mildly coagulated, and hence the body tissue can be kept in a fixed state where its function is stopped while maintaining the cell shape of the body tissue. In this manner, it is possible to prevent a situation that the coagulated surface is peeled off and dropped from the body tissue.

As a device which performs coagulation, hemostasis, incision, and the like of the body tissue by utilizing microwaves as described above, Patent Literature 1 discloses a medical treatment device in which a central electrode and an outer electrode are arranged in such a manner that leading end portions thereof are inclined in the same direction with respect to an axial direction of an outer conductor, and when the outer conductor and a moveable conductor are relatively shifted in the axial direction, the central electrode and the outer electrode are slidingly and relatively shifted along the inclined direction, to thereby cut the body tissue between the central electrode and the outer electrode. In addition, Patent Literature 2 discloses a medical treatment device which is designed so that both blades become parallel to each other at the time of grasping.

CITATION LIST

Patent Literature

Patent Literature 1: JP 2005-21658 A
Patent Literature 2: JP 2007-282666 A

SUMMARY OF INVENTION

Technical Problem

However, in the medical treatment devices described in the conventional technologies as above, an outer cylindrical tube is formed substantially linearly from the front end to the rear end of the medical treatment device in the longitudinal direction. Therefore, there has been a problem that, when the operator attempts to hold the body tissue, particularly, attempts to hold pelvic tissue, his/her visual field cannot be sufficiently ensured. That is, the conventional medical treatment devices have many problems when used in actual clinical medical treatment.

Therefore, the present invention has an object to provide a medical treatment device capable of eliminating inconvenience of the operator's visual field in actual clinical medical treatment.

Solution to Problem

The present invention has been made in view of the above-mentioned problem, and owing to researches of various shapes for a medical treatment device, it has been found that the visual field can be ensured by introducing a curve in the vicinity of an electrode portion of an outer cylindrical tube, as a shape capable of completely achieving functions of grasping, coagulating, and cutting, and further, capable of eliminating problems of the operator's visual field in clinical use. Thus, the present invention has been completed.

The present invention includes the following items:

1. A medical treatment device, including: an electrode portion including a first electrode and a second electrode arranged opposed to the first electrode, the electrode portion having a grasping function, a coagulating function, and a cutting function; an operation portion for executing drive of the grasping function, the coagulating function, and the cutting function of the first electrode and the second electrode; a shaft portion for connecting the electrode portion and the operation portion; a connector portion, which is provided at one end of the operation portion and is connectable to a microwave power source; a conductive rod, which is provided inside the shaft portion, for supplying a microwave to the electrode portion; and an electrode operation rod, which is provided inside the shaft portion, for transmitting an operation force from the operation portion to the electrode portion, the medical treatment device utilizing the microwave being configured to: hold body tissue between the first electrode and the second electrode; coagulate the body tissue by supplying the microwave to the electrodes; and cut the body tissue through a mutual action of the first electrode and the second electrode, in which the shaft portion and the electrode portion are connected to each other with a bent holder.

2. A medical treatment device according to the above-mentioned item 1, in which the bent holder has a structure with divisions, in which divided parts are integrated.

3. A medical treatment device according to the above-mentioned item 1 or 2, in which: the shaft portion includes, on an outer side thereof, an outer cylindrical tube, and, on an inner side thereof, the conductive rod and the electrode operation rod for transmitting the operation force from the operation portion to the electrode portion; and the bent holder is provided continuously from the shaft portion, and includes the outer cylindrical tube, the conductive rod, and the electrode operation rod for transmitting the operation force from the operation portion to the electrode portion.

4. A medical treatment device according to any one of the above-mentioned items 1 to 3, in which in the bent holder, the outer cylindrical tube, the conductive rod, and the electrode operation rod for transmitting the operation force from the operation portion to the electrode portion each have a curving angle substantially the same as a curving angle of the bent holder in the same direction.

5. A medical treatment device according to any one of the above-mentioned items 1 to 4, in which: the conductive rod inside the bent holder is covered with a shielding holder; and the shielding holder has a structure with divisions, in which divided parts are integrated.

6. A medical treatment device according to the above-mentioned item 5, in which the shielding holder for the conductive rod includes a nonconductive member.

7. A medical treatment device according to any one of the above-mentioned items 1 to 6, in which: the electrode operation rod, which is provided inside the bent holder, for transmitting the operation force from the operation portion to the electrode portion is provided inside a guide tube; and at least a curved portion of the guide tube has a flexible tubular structure.

8. A medical treatment device according to the above-mentioned item 7, in which the flexible tubular structure includes a flexible tubular member or a closed coil.

9. A medical treatment device according to any one of the above-mentioned items 1 to 8, in which the electrode operation rod includes a towing wire using a flexible tubular structure as a guide.

10. A medical treatment device according to any one of the above-mentioned items 1 to 9, in which the bent holder has a curving angle in a range of 1 degree to 90 degrees.

11. A medical treatment device according to any one of the above-mentioned items 1 to 10, in which the first electrode and the second electrode include a turnable operation blade and a fixed blade to have an opening and closing function or a sliding function so that the first electrode and the second electrode are relatively shifted.

12. A medical treatment device according to any one of the above-mentioned items 1 to 11, further including a turning member, which is provided at a connection portion between the shaft portion and the operation portion, for rotating a shaft to rotate the bent holder.

13. A medical treatment device according to any one of the above-mentioned items 1 to 12, in which the first electrode and the second electrode are subjected to coating which prevents coagulated tissue from adhering.

14. A medical treatment device according to any one of the above-mentioned items 1 to 13, in which the conductive rod includes a coaxial cable.

15. A medical treatment device according to any one of the above-mentioned items 1 to 14, in which: the first electrode turns in accordance with a front and rear movement of the electrode operation rod and the second electrode is fixed, the first electrode turning about a turning shaft; and the medical treatment device is configured to: hold the body tissue between the first electrode and the second electrode by turning the first electrode; coagulate the body tissue; and shear the body tissue by further turning the first electrode.

Advantageous Effects of Invention

According to the present invention, it is possible to hold the body tissue between the first electrode and the second electrode, coagulate the body tissue by applying microwaves between the first electrode and the second electrode to perform hemostasis, and cut the body tissue through the mutual action of the first electrode and the second electrode. Further, according to the present invention, the first electrode and the second electrode are subjected to coating treatment which prevents adhesion of the body tissue. Therefore, the coagulated body tissue is prevented from adhering, and the coagulation and cutting treatment can be performed successively. In the present invention, the outer cylindrical tube is bent in the vicinity of the electrodes at the front end, or the shaft portion and the electrode portion are connected to each other with the bent holder. Therefore, the operator's visual field can be sufficiently ensured and the body tissue can be easily held and cut. Further, according to the present invention, the shaft portion is turnably supported. Therefore, the directions of the electrodes can be freely changed.

BRIEF DESCRIPTION OF DRAWINGS

FIG. 2B is an X-X cross section of FIG. 2A.

FIG. 3B is a Y-Y cross section of FIG. 3A.

FIG. 4A illustrates a blade edge opening state, FIG. 4B illustrates a state of holding body tissue in accordance with the volume thereof, and FIG. 4C illustrates a blade edge closing state.

DESCRIPTION OF EMBODIMENT

Figure 1:
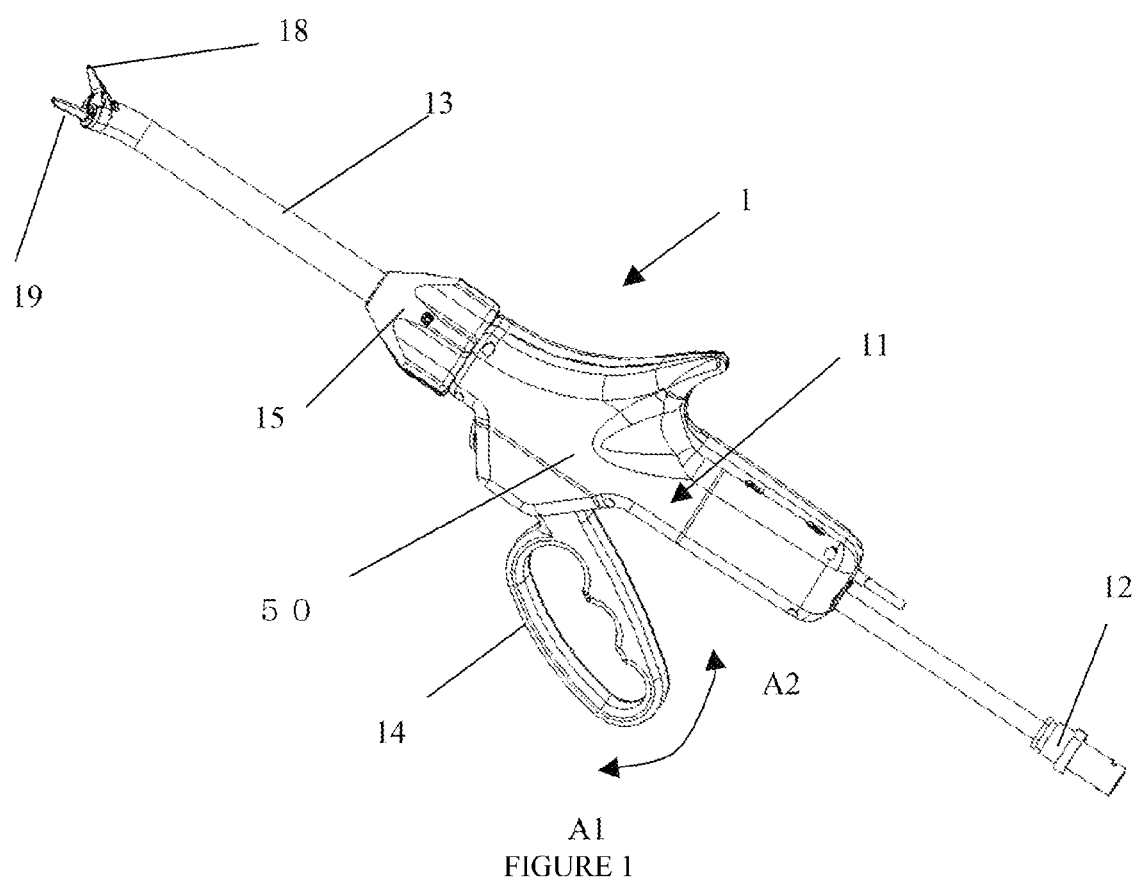
FIG. 1 illustrates an overall structure of a medical treatment device 1 according to a first embodiment of the present invention.

Basic components of a medical treatment device of the present invention are an electrode portion having a grasping function, a coagulating function, and a cutting function, an operation portion including a swingable movable handle, and a shaft portion (also referred to as outer cylindrical tube) for connecting the electrode portion and the operation portion. Additionally, the medical treatment device includes a connector portion which is connectable to a microwave power source, a conductive rod, which is provided inside the shaft portion, for supplying microwaves to the electrode portion, and an electrode operation rod for transmitting an operation force from the operation portion to the electrode portion. Further, a feature of the medical treatment device according to the present invention particularly resides in that the shaft portion and the electrode portion are connected to each other with a bent holder. That is, the medical treatment device has a feature in that the shaft portion (also referred to as outer cylindrical tube) is curved from the vicinity of electrodes at a front end.

In the present invention, the electrode portion includes a first electrode and a second electrode arranged opposed to the first electrode. The shape of the electrode portion is not particularly limited as long as the electrode portion has the grasping function, the coagulating function, and the cutting function, and the electrode portion may have conventionally known shapes in response to its purpose. For example, preferably, the electrode portion may include: a first electrode which turns in accordance with a front-rear movement of the electrode operation rod; and a fixed second electrode arranged opposed to the first electrode, the first electrode having a turning shaft provided on an outer side with respect to a central line between the first electrode and the second electrode, the electrode portion being configured to: hold body tissue between the first electrode and the second electrode by turning the first electrode about the turning shaft by a movable handle; coagulate the body tissue by setting the first electrode and the second electrode to be opposed in parallel to each other and then supplying microwaves to the first electrode and the second electrode (preferably, supplying microwaves to the second electrode); and cut the body tissue through shearing by further turning the first electrode about the turning shaft by the movable handle so that the first electrode and the second electrode are brought into contact with each other from leading ends thereof. Alternatively, in accordance with the device disclosed in JP 2005-21658 A, the leading end portions of the first electrode and the second electrode may be inclined in a curved manner in the same direction with respect to an axial direction of both conductors, and when both the conductors are relatively shifted in the axial direction, the leading end portions of both the conductors may come close to each other to grasp the body tissue and then coagulate the body tissue by the supplied microwaves. Then, both the electrodes may be further slidingly and relatively shifted along the axial direction thereof to cut the body tissue between both the electrodes.

As the contact surface of the electrode portion to the body tissue, a blade shape, a plane form, a round form, a bar shape, a concavo-convex form, and the like may be widely applicable. The electrode portion is a general conductor, and is made of gold-plated or silver-plated copper, gold-plated or silver-plated brass, a copper alloy such as phosphor bronze, and the like. The electrode portion is more preferred to be subjected to coating which prevents the coagulated tissue from adhering when the electrode portion is brought into contact with the body tissue. The coating is performed by gold, Teflon (registered trademark) based member, and the like. In this manner, the processing of coagulation and cutting can be performed successively without adhesion of the coagulated body tissue.

In the present invention, the operation portion including the swingable movable handle refers to a part in which, through operation of, for example, pulling and gripping, the drive of the grasping function and the cutting function of the first electrode and the second electrode is executed. Further, a swinging movement may be caused by applying load to the operation portion such as the movable handle, and in order to transmit this swinging movement to the electrode operation rod in a manner being converted into a front-rear movement, there may be used a widely known mechanism, for example, a slider-crank mechanism. The operation portion includes, as main components, for example, a movable handle portion and a main body portion including a fixed handle.

The medical treatment device of the present invention includes a cylindrical-tube shaped shaft portion as a part connecting the operation portion and the electrode portion. The shaft portion is also represented as an outer cylindrical tube in the following embodiment and the drawings. The outer cylindrical tube serves as a cover. The electrode operation rod is housed in the outer cylindrical tube, and further, a conductive rod for transmitting the microwaves is housed therein. The length of the shaft portion is substantially about 10 to 25 cm, but is not particularly limited as long as the length is sufficient to connect the operation part for the operator and the electrode portion corresponding to the contact part with the surgery target tissue and the like. The overall structure of the medical treatment device of the present invention is preferred to be made of a nonmagnetic metal such as phosphor bronze. With this, the medical treatment device can be preferably used even in an environment under the magnetic field caused by, for example, an MR system.

In the present invention, the electrode operation rod means an operation shaft which transmits a swinging movement caused by the operation portion as a front-rear movement to the electrode portion, particularly, to the movable first electrode. The electrode operation rod is formed of a general wire, and transmits the operation force from the operation portion to the electrode portion. The outer side of the electrode operation rod is guided by a guide tube. The guide tube is preferred to be formed of a nonmagnetic member (for example, coil made of Teflon (registered trademark), phosphor bronze, or the like). Note that, in the following embodiment and the drawings, opening/closing is described as a specific example of the operation, and hence the electrode operation rod is also referred to as an electrode opening/closing rod.

In the present invention, the conductive rod transmits the microwaves from a microwave radiation source via the connector portion to the electrode portion. The conductive rod is preferred to be formed of a coaxial cable, and an outer side thereof is covered with a shielding holder. The shielding holder is preferred to be formed of a nonconductive member (for example, polyether ether ketone resin).

The coaxial cable includes a central electrode which is a conductor made of, for example, phosphor bronze, a shielding tube which is an insulator made of, for example, Teflon (registered trademark) and covers the central electrode, and a grounded pipe which is a conductor made of, for example, brass. In the present invention, microwaves of 900 to 6,000 MHz may be equivalently used.

The phrase "the shaft portion and the electrode portion are connected to each other with a bent holder," which is the feature of the present invention, means that, in other words, the shaft portion (also referred to as the outer cylindrical tube) is curved in the vicinity of the electrodes at the front end, that is, a neck portion. The length of the bent holder is substantially 3 to 6 cm, and an angle thereof is 1 degree to 90 degrees, preferably 5 degrees to 85 degrees, more preferably 10 degrees to 80 degrees. The bent holder may correspond to a curved portion formed integrally with the shaft portion, and in some cases, means a portion of the same outer cylindrical tube, which is curved in the vicinity of the electrodes at the front end, that is, the neck portion. However, because the manufacturing is simple, the bent holder may be prepared separately from the shaft portion, and may be provided in the vicinity of the electrodes at the front end, that is, the neck portion as a separate bent holder.

The bent holder has a tubular shape, and includes therein the conductive rod covered with the shielding holder and the electrode operation rod provided inside the guide tube. Definitions of respective members are the same as those described above. Here, the bent holder is preferred to have a structure with divisions, in which divided parts are integrated, more preferred to have a structure with two to four divisions, in which two to four divided parts are integrated, and still more preferred to have the structure with two divisions. When the bent holder is integrated with the shaft portion, the bent holder is preferred to have a structure with divisions, in which divided parts including the outer cylindrical tube of the shaft portion are integrated, more preferred to have a structure with two to four divisions, in which two to four divided parts are integrated, and still more preferred to have the structure with two divisions. More generally, it suffices that only the bent holder has this structure.

The conductive rod covered with the shielding holder and the electrode operation rod provided inside the guide tube, which are provided inside the bent holder, have a curving angle substantially the same as the curving angle of the bent holder in the same direction.

The shielding holder covering the conductive rod to be provided inside the bent holder is made of the material described above, and is preferred to have a structure with divisions, in which divided parts are integrated, more preferred to have a structure with two to four divisions, in which two to four divided parts are integrated, and still more preferred to have the structure with two divisions. The shielding holder is a nonconductive member.

The electrode operation rod (in the following embodiment and the drawings, described as electrode opening/closing rod) inside the bent holder is provided inside the guide tube. At least a curved portion of the guide tube has a flexible tubular structure. Preferably, the flexible tubular structure is a flexible tubular member or a closed coil. The electrode operation rod functions as a towing wire using the flexible tubular structure as a guide.

In the medical treatment device of the present invention, the bent holder can be freely rotated so that the operator can easily perform the surgery treatment in upper, lower, and lateral directions. In order to obtain this rotation, a turning member may be provided at a connection portion between the shaft portion and the operation portion, for rotating a shaft to rotate the bent holder.

Embodiment

Figure 2:
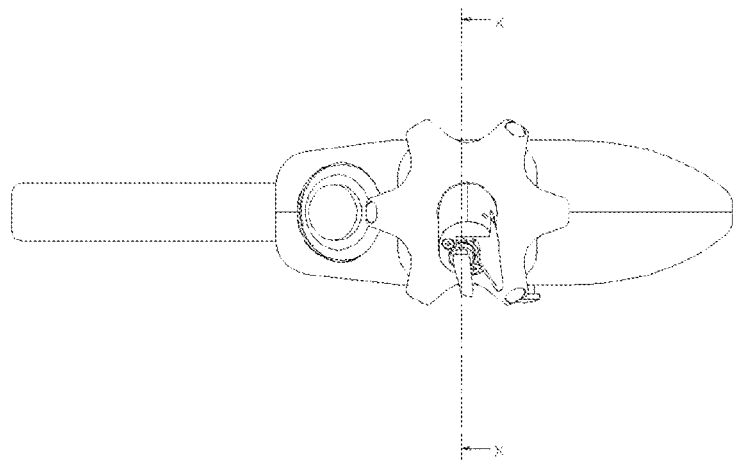
FIG. 2 illustrate a cross section of an electrode portion and a bent holder.
Figure 2:
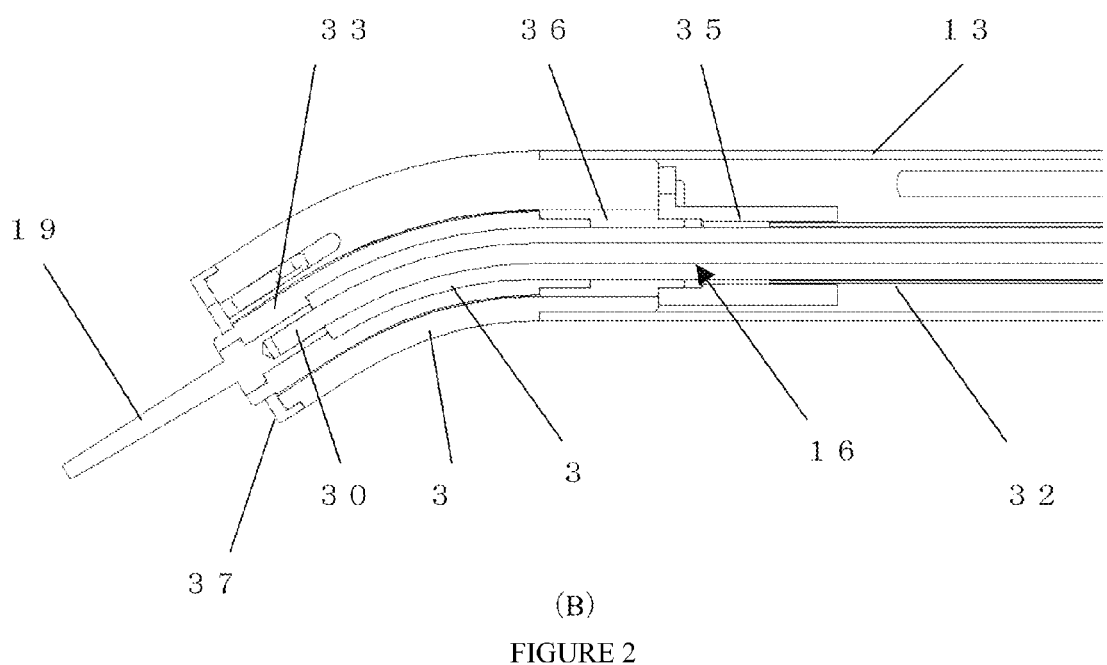
Figure 3:
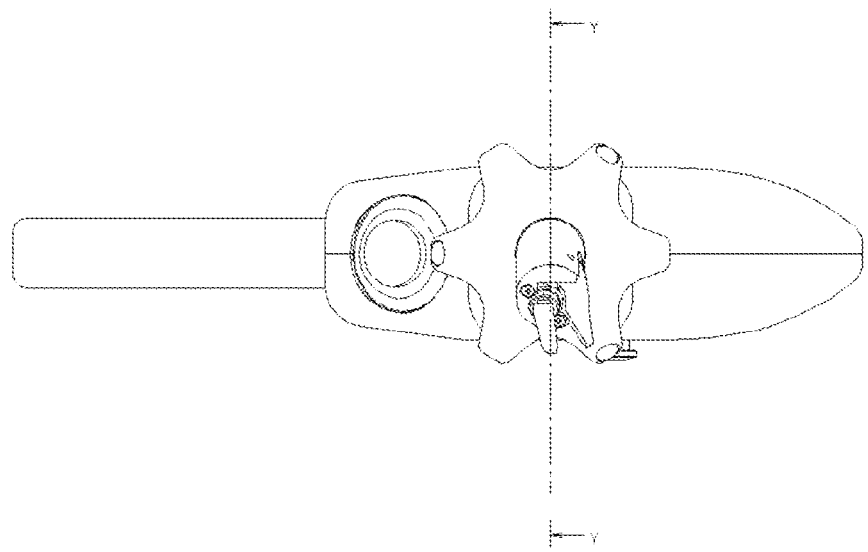
FIG. 3 illustrate a cross section of the electrode portion and the bent holder.
Figure 3:
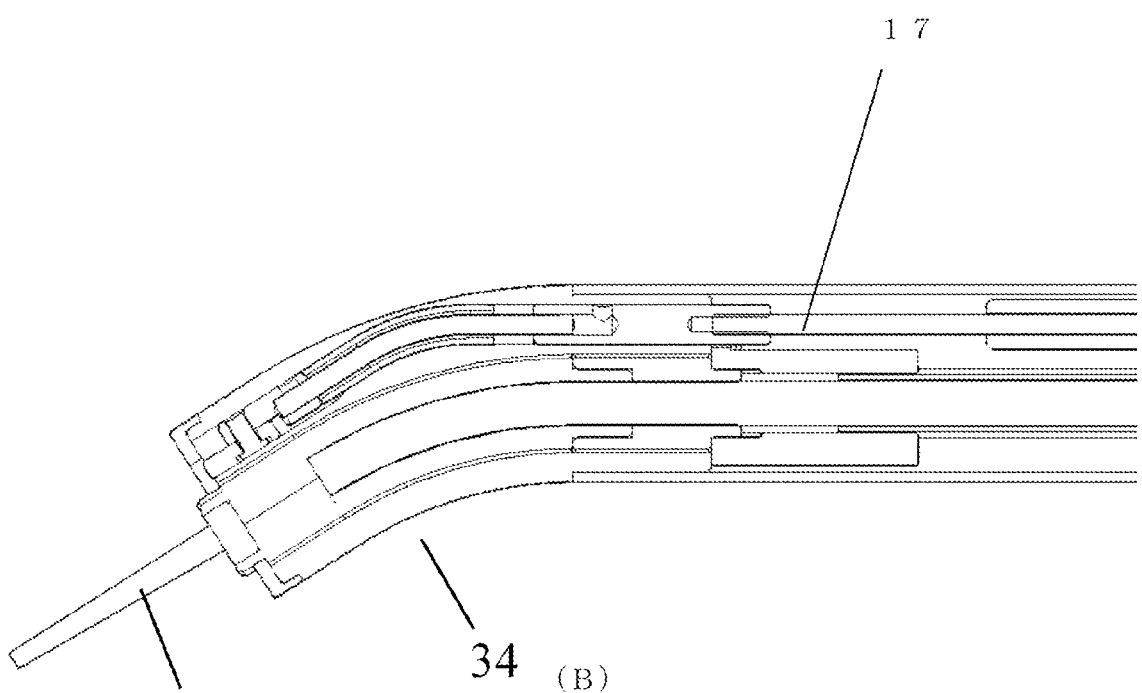

Hereinafter, an embodiment of the present invention is described with reference to the drawings. FIG. 1 illustrates an overall structure of a medical treatment device 1 according to a first embodiment of the present invention. Further, FIG. 2(B) is an X-X cross section of FIG. 2(A). FIG. 3(B) is a Y-Y cross section of FIG. 3(A).

As illustrated in FIG. 1, in the medical treatment device 1, reference symbol 11 represents a main body portion. At the rear end of the main body portion 11, a connector 12 is provided. Via the connector 12, microwaves of, for example, 2.45 GHz band are supplied. From the main body portion 11, an outer cylindrical tube 13 is led out. Inside the outer cylindrical tube 13, there are housed, as illustrated in FIG. 2(B), a conductive rod 16 for transmitting microwave electric power from the connector 12, and as illustrated in FIG. 3(B), an electrode opening/closing rod 17 for transmitting the movement of a movable handle 14 to an upper blade electrode 18 to open/close an electrode.

On the lower side of the main body portion 11, the movable handle 14 is swingably mounted. Inside the main body portion 11, as described later, there is provided a slider-crank mechanism for converting a swinging movement of the movable handle 14 into a front-rear movement of the electrode opening/closing rod 17. Further, the main body portion 11 is provided with a turning member 15. By rotating the turning member 15, the outer cylindrical tube 13 firmly fixed to the turning member 15 can be turned to a desired angle.

Figure 4:
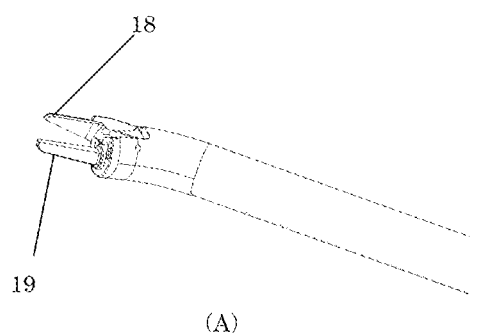
FIG. 4 illustrate an electrode portion 2. An upper blade electrode (first electrode) 18 and a lower blade electrode (second electrode) 19 are provided opposed to each other.
Figure 4:
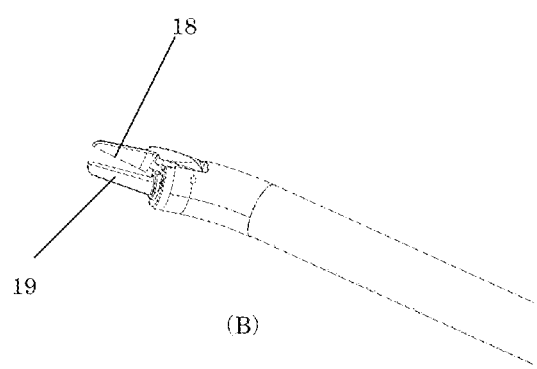
Figure 4:
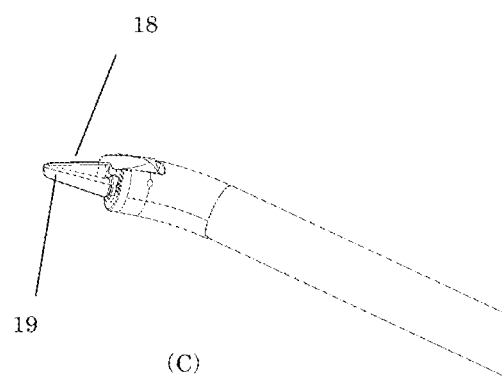

At the front end of the outer cylindrical tube 13, as illustrated in FIG. 4, the upper blade electrode (first electrode) 18 and a lower blade electrode (second electrode) 19 are provided opposed to each other. The lower blade electrode 19 is fixed. The upper blade electrode 18 is turnably provided. When the movable handle 14 is swung, the electrode opening/closing rod 17 (see FIG. 3) inside the outer cylindrical tube 13 move in the front-rear direction, to thereby cause the upper blade electrode 18 to turn. To the lower blade electrode 19, the microwaves from the connector 12 are supplied via the conductive rod 16.

When a force is not applied to the movable handle 14, the movable handle 14 is biased in the arrow A1 direction in FIG. 1. At this time, as illustrated in FIG. 4(A), the upper blade electrode 18 is separated from the lower blade electrode 19, which corresponds to a blade edge opening state. When the movable handle 14 is swung in the arrow A2 direction, as illustrated in FIG. 4(B), the upper blade electrode 18 approaches the lower blade electrode 19. When the movable handle 14 is further swung in the arrow A2 direction, as illustrated in FIG. 4(C), the upper blade electrode 18 further approaches the lower blade electrode 19 from the blade edge thereof, resulting in a blade edge closing state.

The medical treatment device 1 according to the first embodiment of the present invention is used as follows. First, the upper blade electrode 18 and the lower blade electrode 19 are set to the blade edge opening state as illustrated in FIG. 4(A), and leading ends of the upper blade electrode 18 and the lower blade electrode 19 are guided to the target body tissue. After the leading ends of the upper blade electrode 18 and the lower blade electrode 19 are guided to the body tissue as a target of the treatment, the movable handle 14 is swung in the arrow A2 direction. When the movable handle 14 is swung in the arrow A2 direction, the upper blade electrode 18 is closed, which makes it possible to hold the body tissue between the upper blade electrode 18 and the lower blade electrode 19.

While holding the body tissue between the upper blade electrode 18 and the lower blade electrode 19 in such a blade edge state as illustrated in FIG. 4(B) in accordance with the volume of the body tissue, the microwave electric power is supplied between the upper blade electrode 18 and the lower blade electrode 19. With this, due to the near electromagnetic field generated by the microwave electric power, which is formed between the upper blade electrode 18 and the lower blade electrode 19, dielectric heat is generated in the body tissue. With this dielectric heat, the body tissue is coagulated.

Then, from the coagulation treatment state, the movable handle 14 is further gripped so that the movable handle 14 is further swung in the arrow A2 direction. When the movable handle 14 is further swung, the upper blade electrode 18 and the lower blade electrode 19 are set to the blade edge closing state as illustrated in FIG. 4(C), thereby cutting the body tissue through shearing.

As described above, the medical treatment device 1 of the first embodiment of the present invention enters, by operating the movable handle 14, as illustrated in FIGS. 4(A) to 4(C), the blade edge opening state, the state of holding the body tissue in accordance with the volume thereof, and the blade edge closing state. With this, it is possible to hold the body tissue between the upper blade electrode 18 and the lower blade electrode 19, coagulate the body tissue by setting the upper blade electrode 18 and the lower blade electrode 19 to a blade edge parallel state and then applying the microwaves between the upper blade electrode 18 and the lower blade electrode 19, and cut the body tissue through shearing by setting the upper blade electrode 18 and the lower blade electrode 19 to the blade edge closing state.

Further, the overall structure of the medical treatment device 1 of the present invention is made of a nonmagnetic metal such as phosphor bronze. With this, the medical treatment device 1 can be preferably used even in an environment under the magnetic field caused by, for example, an MR system.

As illustrated in FIGS. 2(B) and 3(B), inside the outer cylindrical tube 13, the conductive rod 16 and the electrode opening/closing rod 17 are housed. The conductive rod 16 includes a central electrode 30 which is a conductor made of, for example, phosphor bronze, a shielding tube 31 which is made of an insulator (for example, Teflon (registered trademark)) and covers the central electrode, and a pipe (grounded pipe) 32 which is a conductor made of, for example, brass.

Onto the front end of the conductive rod 16, a shielding holder 33 made of, for example, a polyether ether ketone resin is mounted, and the lower blade electrode 19 is fixed to the shielding holder 33. The central electrode 30 of the conductive rod 16 and the lower blade electrode 19 are electrically connected to each other. Further, onto the outer periphery of the shielding holder 33, a holder 34 is mounted. The holder 34 is conductive and made of, for example, phosphor bronze. The grounded pipe 32 of the conductive rod 16 and the holder 34 are electrically connected to each other via a clasp 35.

Figure 5:
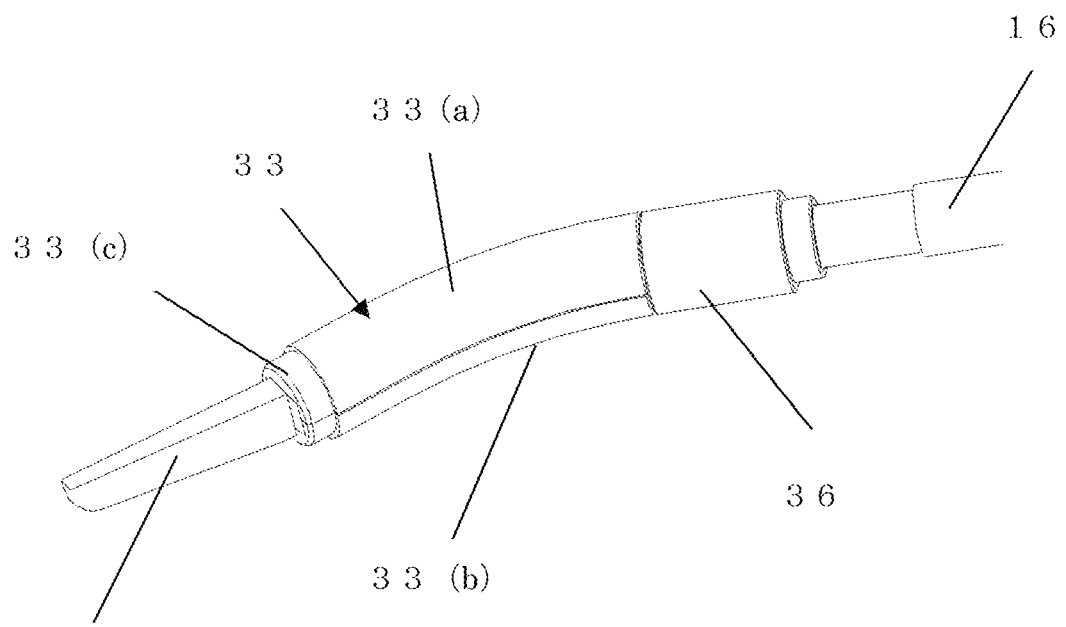
FIG. 5 illustrates the lower blade electrode 19.
Figure 9:
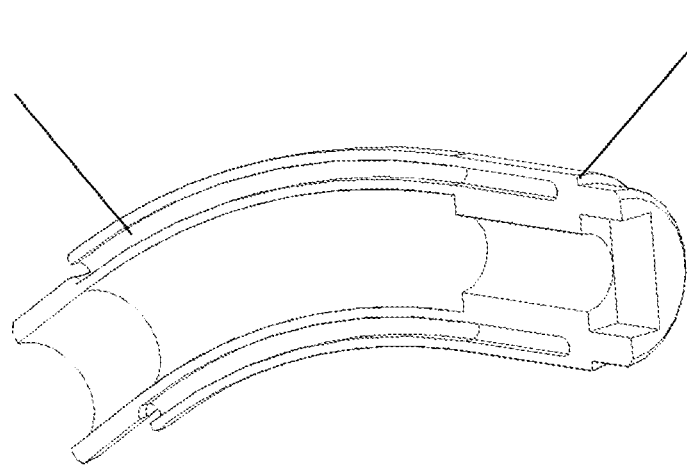
FIG. 9 illustrate shapes of two divided parts 33(a) and 33(b) of the shielding holder 33. Note that, the part 33(a) is provided with a semicircular groove 41, and the part 33(b) is provided with a semicircular flange 42. Note that, the semicircular groove 41 and the semicircular flange 42 match with each other.
Figure 9:
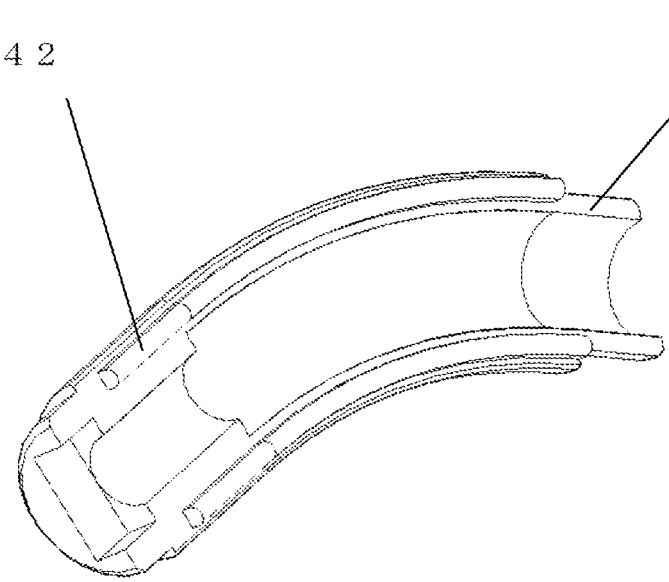

As illustrated in FIG. 5, the shielding holder 33 is divided into two shielding holder parts 33(a) and 33(b), which are adhered to each other while sandwiching the lower blade electrode 19 in a state of being connected to the conductive rod 16 with solder. Further, a shielding cap 36 is adhered at the same time. FIGS. 9(A) and 9(B) illustrate shapes of the two divided parts 33(a) and 33(b) of the shielding holder 33. The part 33(a) is provided with a semicircular groove 41, into which a semicircular flange 42 provided to the part 33(b) is fitted in a manner matching with each other.

Figure 6:
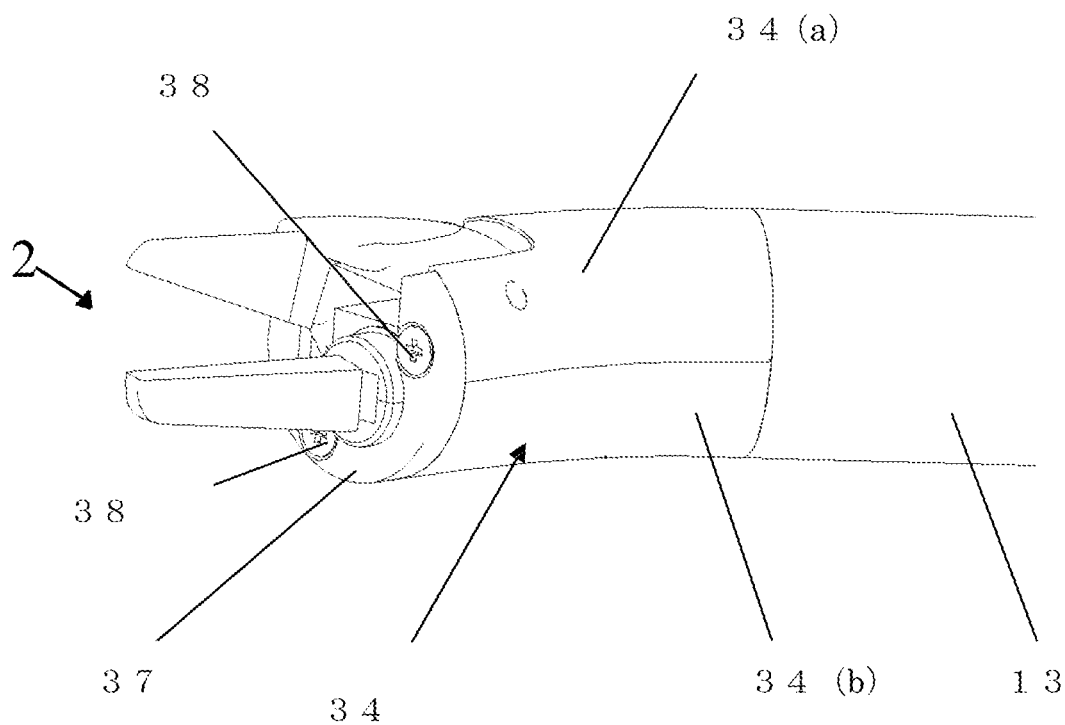
FIG. 6 illustrates the electrode portion and the bent holder portion. A shielding holder 33 is covered with a bent holder 34 which is divided into two parts 34(a) and 34(b), and is fixed by an outer cylindrical tube 13.

The shielding holder 33 in this fitted state is, as illustrated in FIG. 6, covered with the holder 34 which is divided into two holder parts 34(a) and 34(b), and is fixed by the outer cylindrical tube 13. A fixing method therefor is carried out by, for example, laser welding.

Figure 10:
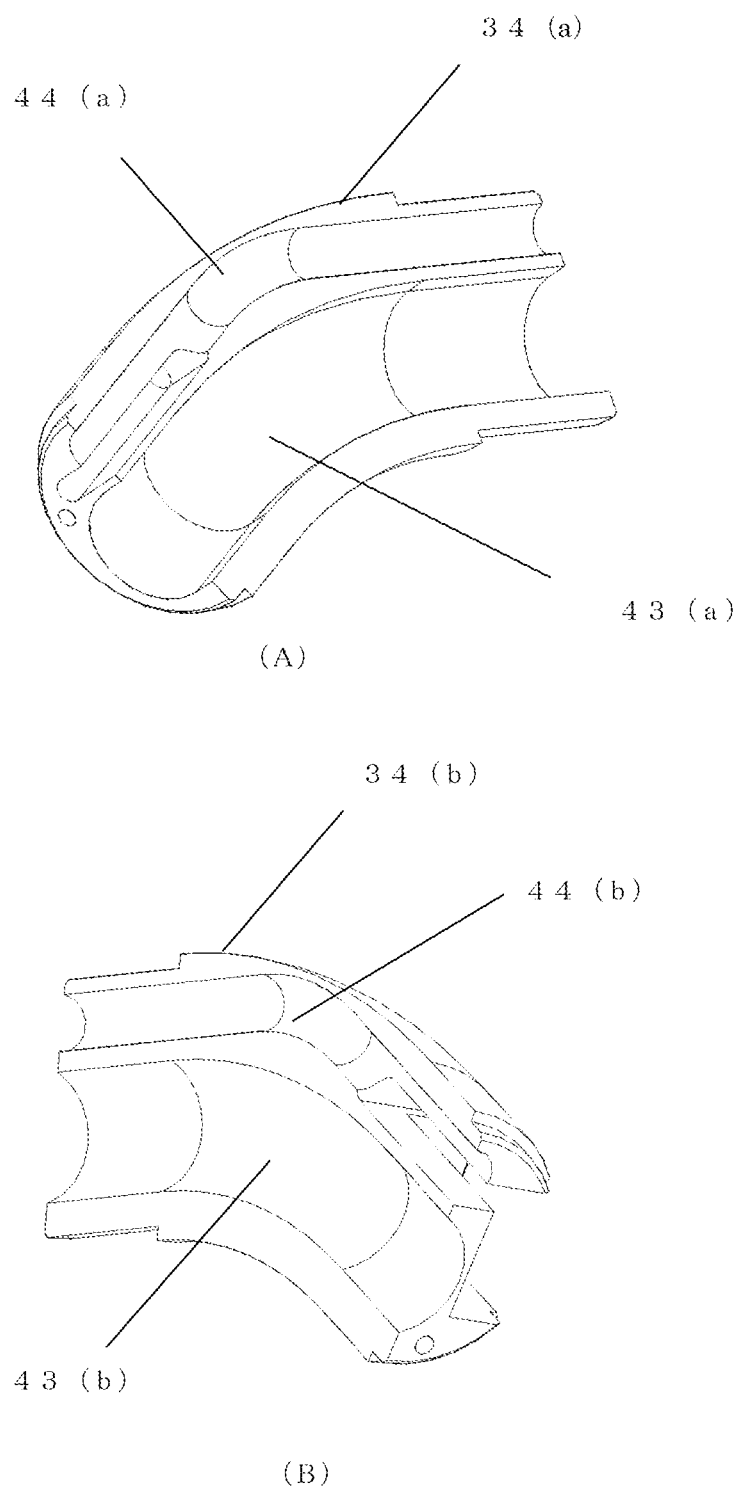
FIG. 10 illustrate shapes of the two divided parts 34(a) and 34(b) of the bent holder 34.

FIGS. 10(A) and 10(B) illustrate shapes of the two divided holder parts 34(a) and 34(b) of the holder 34. The parts 34(a) and 34(b) are provided with a semicircular groove 43(a) and a semicircular groove (b), respectively, in which the shielding holder 33 is housed. Further, the parts 34(a) and 34(b) are provided with semicircular grooves 44(a) and 44(b), respectively, in which the electrode opening/closing rod 17 is housed.

Figure 7:
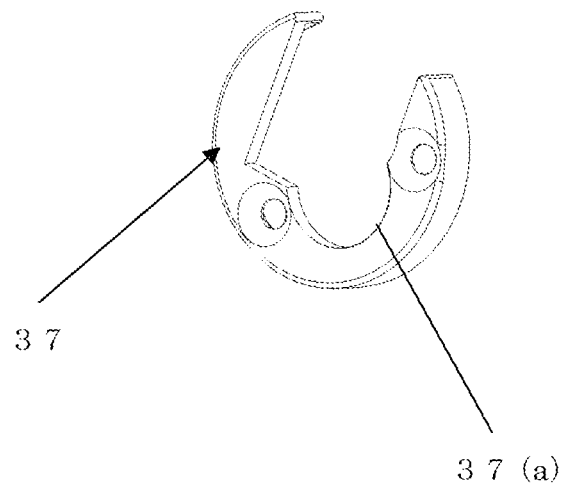
FIG. 7 illustrates a fixation cap 37 to be fixed to the holder 34.

FIG. 7 illustrates a fixation cap 37 to be fixed to the holder 34. The fixation cap 37 is provided with a hole 37(a) having a notch, and is fixed to the holder 34 with screws 38 (two screws). Further, the hole 37(a) is formed so that a neck portion 33(c) of the shielding holder 33 is fittable thereto, to thereby obtain a firmer fixation.

The structure in which each of the shielding holder 33 and the holder 34 is divided into two parts as described above is introduced in order to realize the feature that this part is bent.

Figure 8:
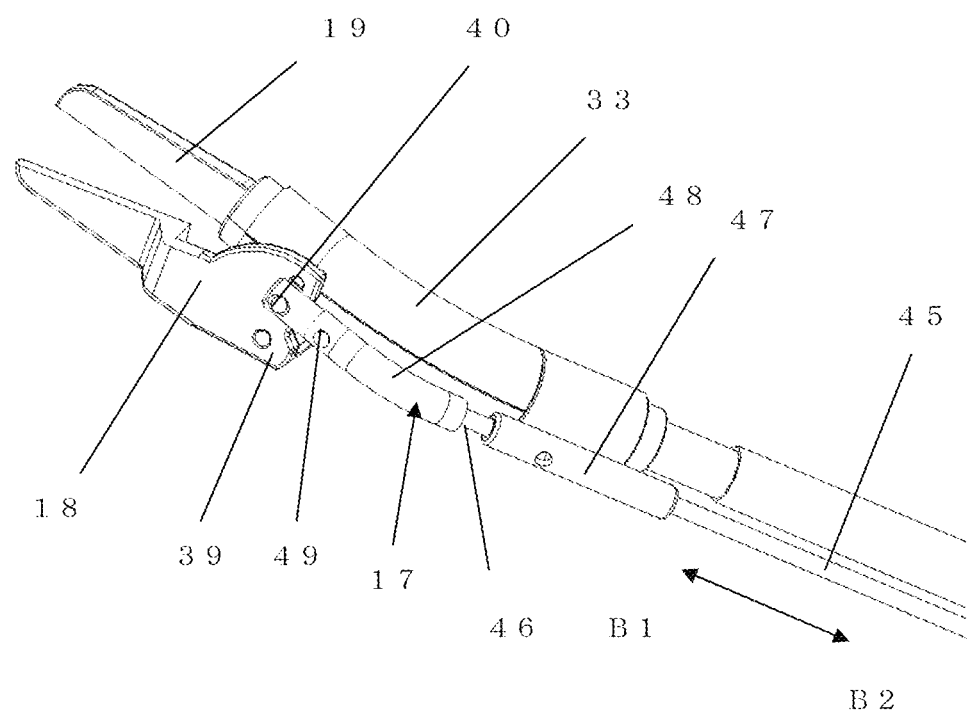
FIG. 8 illustrates the electrode portion 2, and a conductive rod and an electrode operation rod provided inside the bent holder. The upper blade electrode 18 is turnably and pivotably supported by a turning shaft 39, which is pivotably supported by the holder 33. Further, an end of an electrode opening/closing rod 17 is connected to the upper blade electrode 18 at a mounting position 40.

Meanwhile, as illustrated in FIG. 8, the upper blade electrode 18 is turnably and pivotably supported by a turning shaft 39, which is pivotably supported by the holder 33. Further, an end of the electrode opening/closing rod 17 is connected to the upper blade electrode 18 at a mounting position 40.

Figure 11:
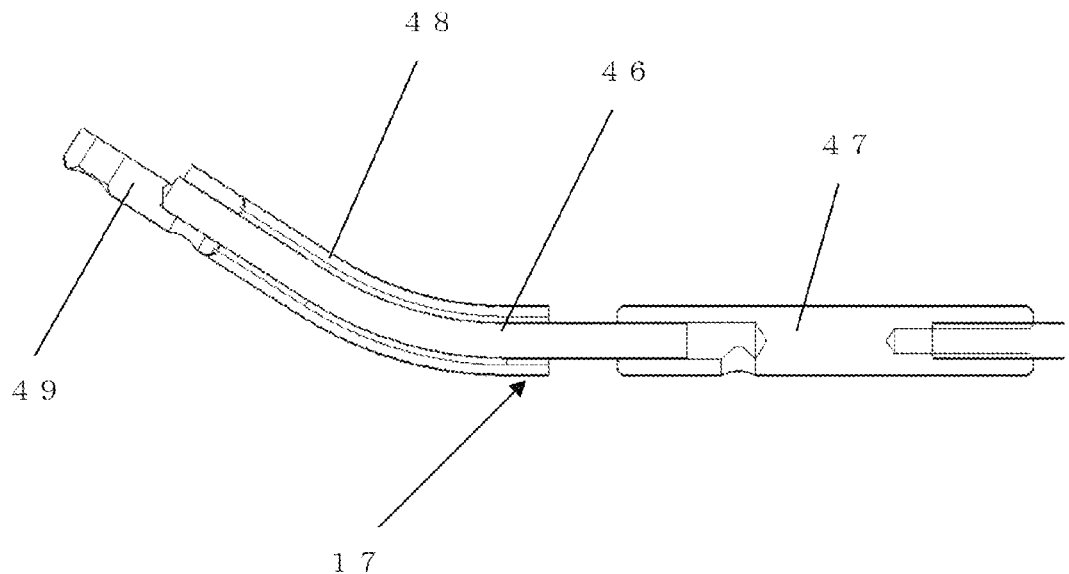
FIG. 11 is a sectional view of the electrode opening/closing rod 17.

As illustrated in FIG. 11, the electrode opening/closing rod 17 includes a towing rod 45, a flexible towing wire 46, a connection tube 47 for connecting those members, a flexible guide tube 48 for protecting the towing wire 46 from being disconnected due to friction, and a link pin 49 for turning the upper blade electrode 18. Note that, the flexible towing wire 46 is formed of a nonmagnetic metal wire rope made of, for example, phosphor bronze. The guide tube 48 is formed of a nonmagnetic coil made of, for example, Teflon (registered trademark) or phosphor bronze.

When the movable handle 14 is swung, as illustrated by arrows B1 and B2 in FIG. 8, the electrode opening/closing rod 17 moves in the front-rear direction. When the electrode opening/closing rod 17 moves in the front-rear direction, the upper blade electrode 18 is turned to perform opening and closing. The upper blade electrode 18 is turned about the turning shaft 39. With this, as illustrated in FIGS. 4(A) to 4(C), the blade edge opening state, a blade edge approaching state, and the blade edge closing state are obtained.

As described above, in the first embodiment of the present invention, from the blade edge opening state, the body tissue can be held between the upper blade electrode 18 and the lower blade electrode 19 in accordance with the volume of the body tissue, and then the microwaves can be applied. After that, the application of the microwaves is stopped, and then the body tissue can be cut with the upper blade electrode 18 and the lower blade electrode 19 from the blade edges thereof as the blade edge closing state.

Note that, the upper blade electrode 18 and the lower blade electrode 19 are subjected to coating of Teflon (registered trademark) based member or gold, which prevents adhesion. In this manner, the processing of coagulation and cutting can be performed successively without adhesion of the coagulated body tissue.

Next, description is made of the slider-crank mechanism for converting a swinging movement of the movable handle 14 into a front-rear movement of the electrode opening/closing rod 17.

Figure 12:
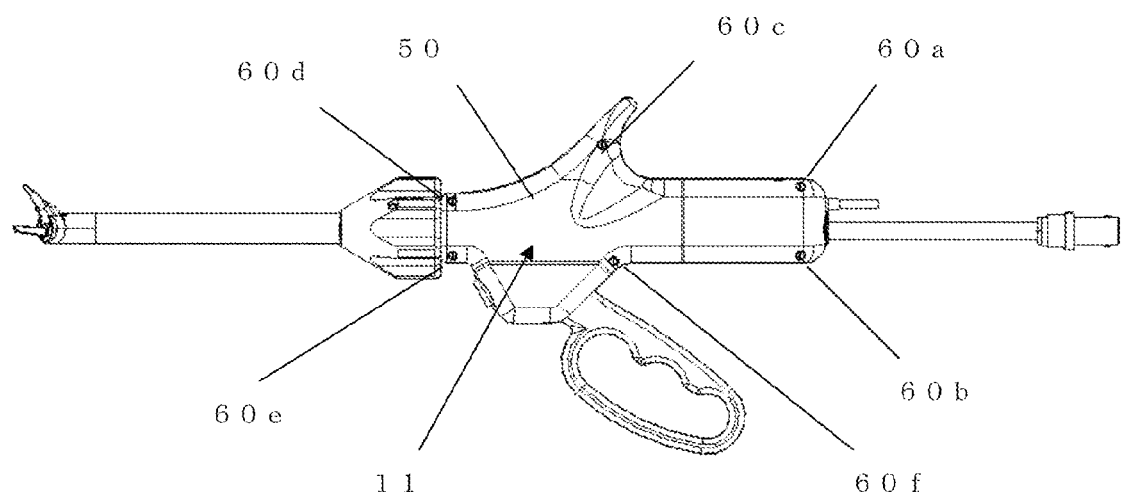
FIG. 12 is a side view of the medical treatment device 1, illustrating a main body portion 11 covered with a main body cover 50 made of a resin.
Figure 13:
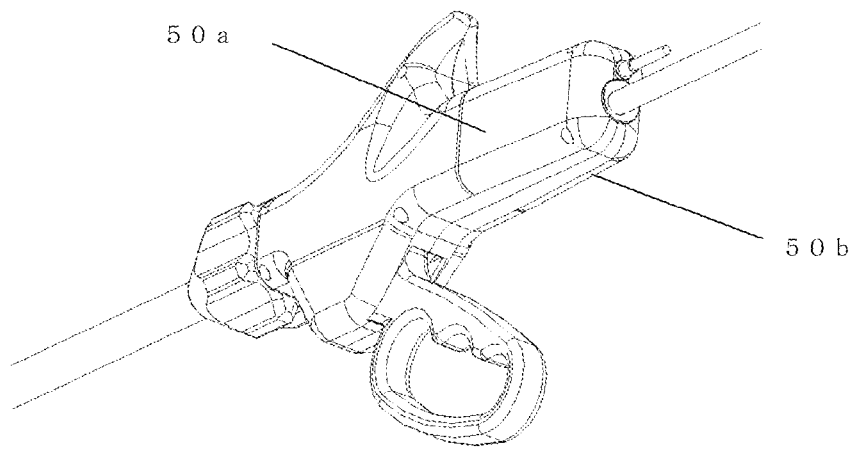
FIG. 13 is a lower perspective view of the medical treatment device 1, illustrating the main body portion 11. The main body cover 50 is formed of two divided parts 50a and 50b.
Figure 14:
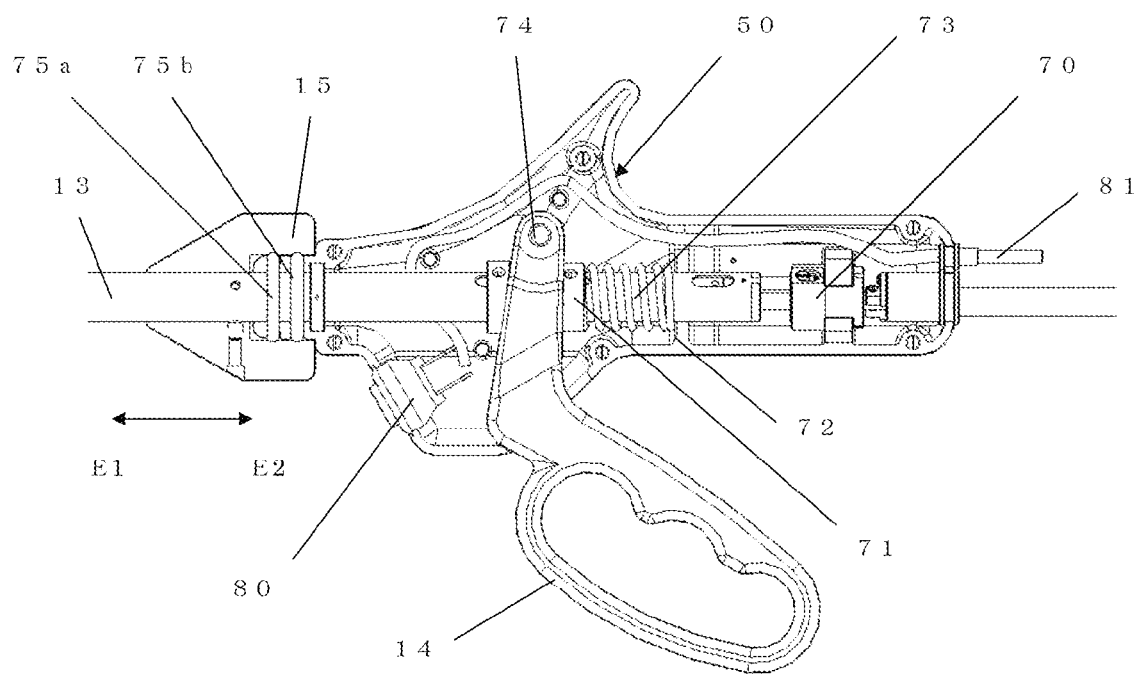
FIG. 14 illustrates an inner structure of the main body portion 11.

In FIG. 12, the main body portion 11 is covered with a main body cover 50 made of a resin. As illustrated in FIG. 13, the main body cover 50 is formed of two divided parts 50a and 50b. The parts 50a and 50b are threadably fixed with screws 60a, 60b, 60c, 60d, 60e, and 60f. When the part 50a is detached from the main body cover 50 of the main body portion 11, as illustrated in FIG. 14, the inner structure of the main body portion 11 appears. As illustrated in FIG. 12, apart of the main body portion 11 functions as a fixed handle 14-2.

In FIG. 14, the outer cylindrical tube 13 is inserted through the turning member 15, and an end of the outer cylindrical tube 13 is fixed to a cylindrical mounting member 70. The turning member 15 is formed so that the turning member 15 does not easily turn without the operator's intent by the frictional resistance of rings 75a and 75b made of rubber (silicon, fluorine rubber, and the like). The outer cylindrical tube 13 is turnably supported inside the main body portion 11 by the turning member 15 and the cylindrical mounting member 70. Further, onto the outer periphery of the outer cylindrical tube 13, a cylindrical member 71 is slidably mounted. The cover 50 is provided with a partition wall 72, and a coil spring 73 is provided between the partition wall 72 and the cylindrical member 71. The coil spring 73 biases the cylindrical member 71 in the arrow E1 direction.

Figure 15:
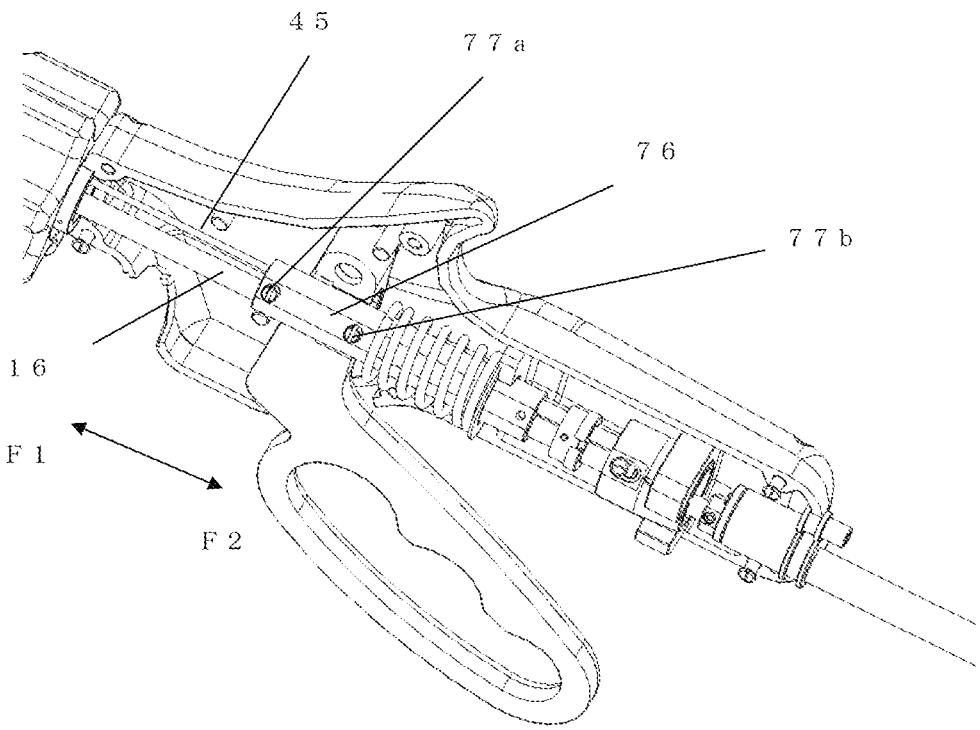
FIG. 15 illustrates an inner structure of the outer cylindrical tube 13 inside the main body portion 11.
Figure 16:
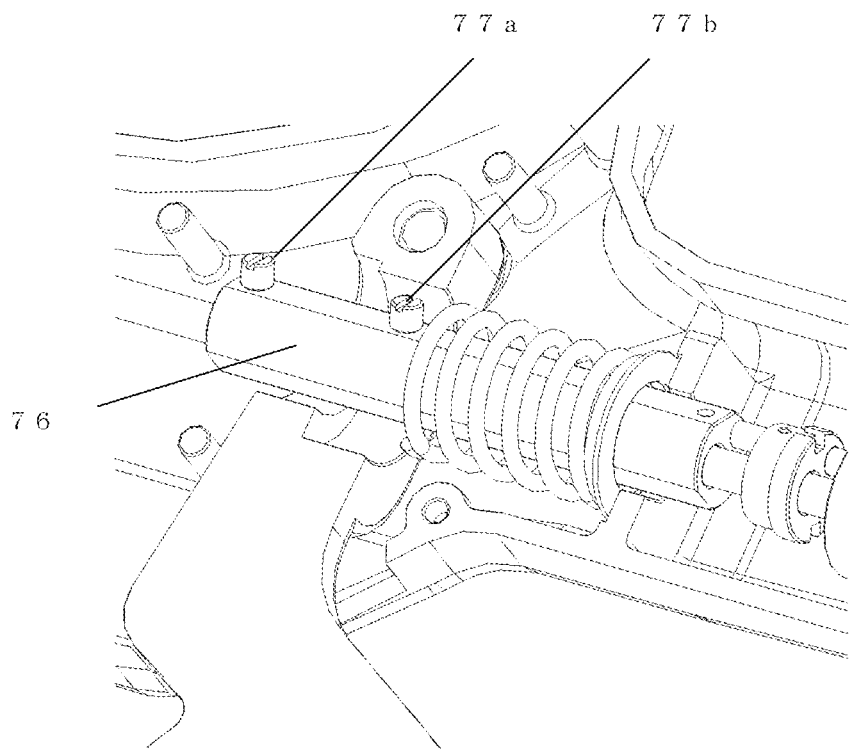
FIG. 16 illustrates a state in which sliding pins 77a and 77b are fixed to a sliding bar 76 inside the main body portion 11.
Figure 17:
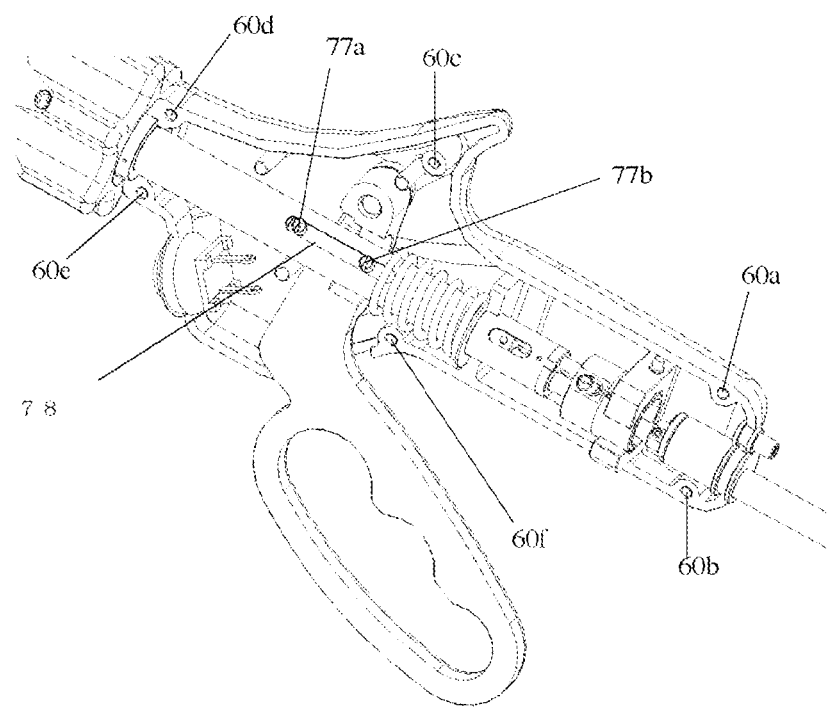
FIG. 17 illustrates a state in which the sliding pins 77a and 77b move while being guided by a long hole 78 provided in the outer cylindrical tube 13 inside the main body portion 11.

FIG. 15 illustrates the inner structure of the outer cylindrical tube 13 inside the main body portion 11. A sliding bar 76 has a hole with a diameter larger than a diameter of the conductive rod 16, and is slidable without connection to the conductive rod 16. The sliding bar 76 is connected to the towing rod 45, and when the sliding bar 76 moves in directions of the arrows F1 and F2, the towing rod 45 simultaneously moves. With this movement, the upper blade electrode 18 turns to hold the body tissue. Further, the sliding bar 76 has sliding pins 77a and 77b fixed thereto (see FIG. 16). As illustrated in FIG. 17, the sliding pins 77a and 77b move while being guided by a long hole 78 provided in the outer cylindrical tube 13.

Figure 18:
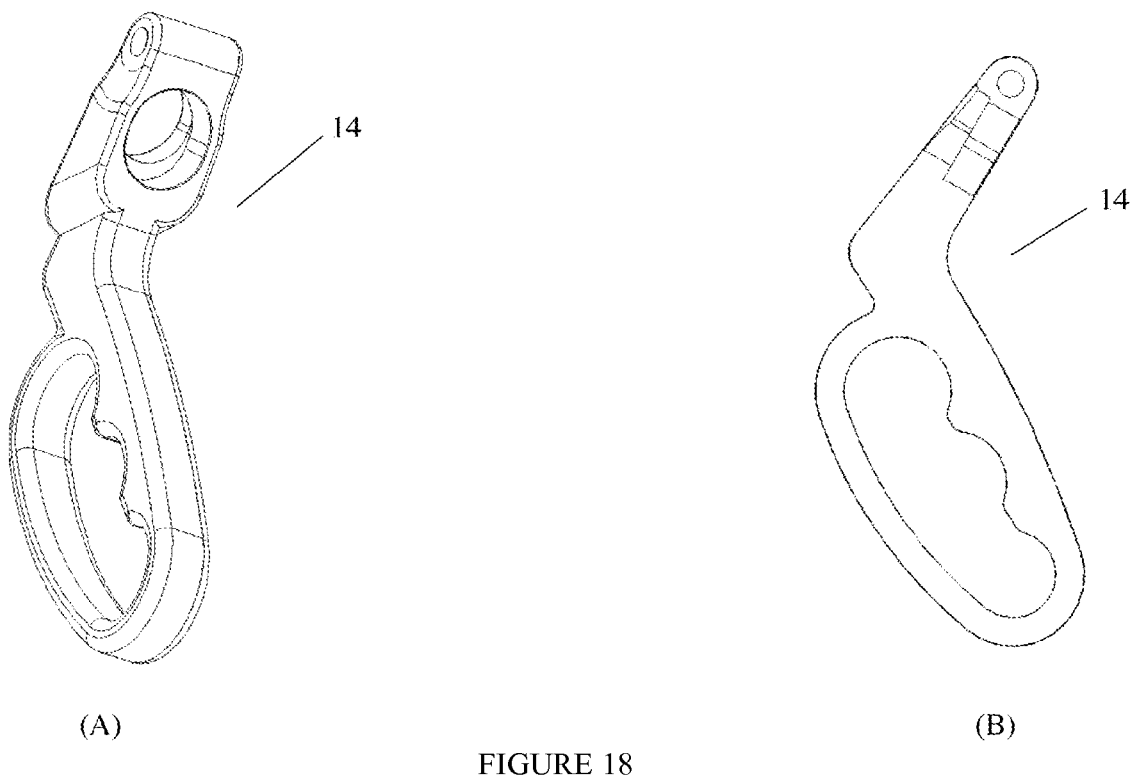
FIG. 18 illustrate an external view A and a sectional view B of a movable handle 14.
Figure 19:
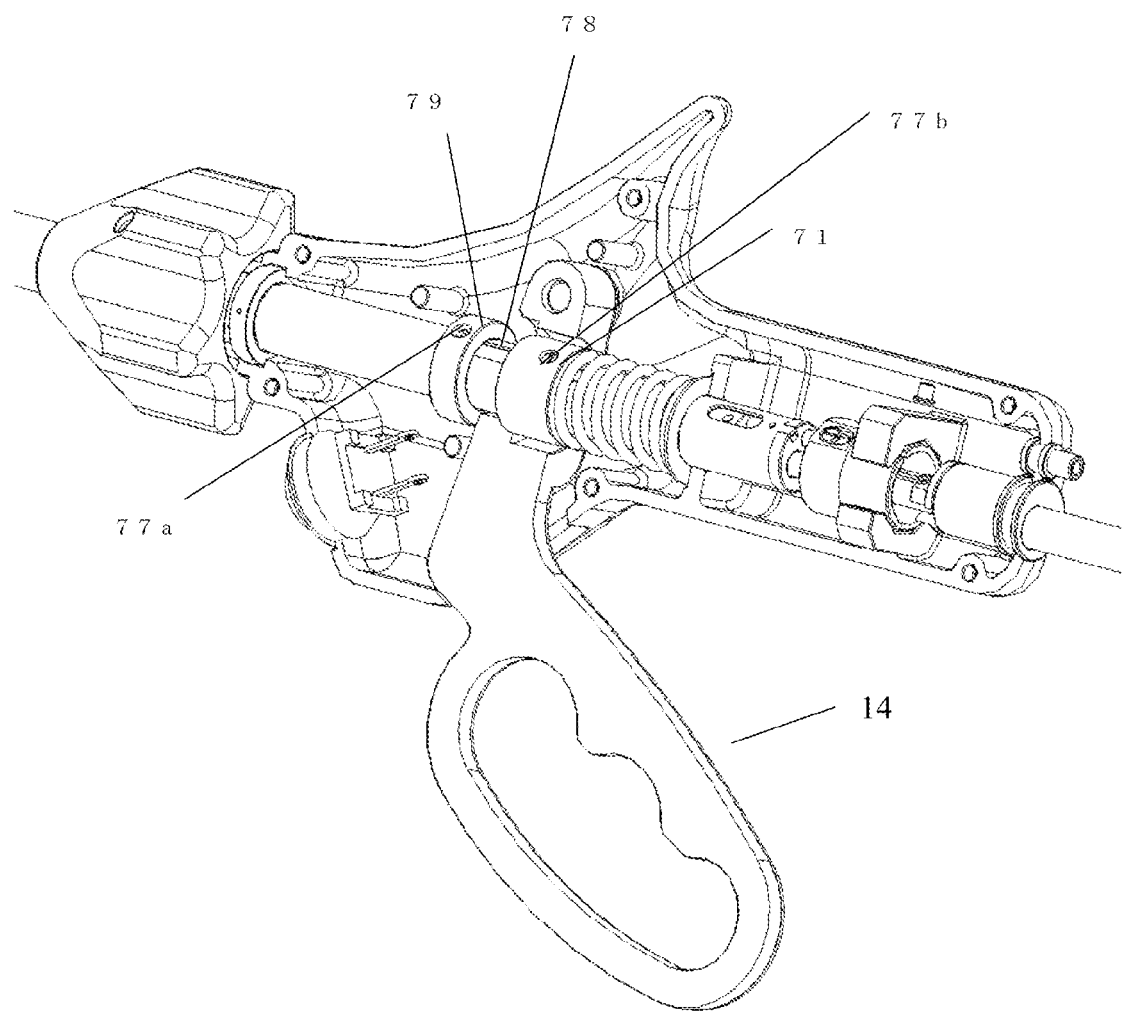
FIG. 19 illustrates structures of the movable handle 14, a cylindrical member 71, and a cylindrical member 79.

FIG. 18 illustrate an external view and a sectional view of the movable handle 14. FIG. 19 illustrates structures of the movable handle 14, the cylindrical member 71, and a cylindrical member 79. The cylindrical member 71 is connected to the sliding bar 76 via the sliding pin 77b. Further, the cylindrical member 79 is connected to the sliding bar 76 via the sliding pin 77a. Note that, the movable handle 14 is turnably and pivotably supported about a turning fulcrum 74 (see FIG. 14). Further, in FIG. 14, there is provided a switch 80 for applying the microwaves, and with the switch operation, a coagulation command is issued via a signal line 81 to a microwave radiation device.

As described above, by swinging the movable handle 14, via the cylindrical members 71 and 79, the sliding pins 77a and 77b are guided in the long hole 78 and the sliding bar 76 (see FIG. 15) moves in the E1-E2 direction of FIG. 14. Further, by the movement of the sliding bar 76, the upper blade electrode 18 turns to hold the body tissue together with the lower blade electrode 19. When the switch 80 is pressed, the microwaves are applied to coagulate the body tissue, and further, the movable handle 14 is swung to cut the body tissue.

The present invention is not limited to the above-mentioned embodiment, and various modifications and applications may be made thereto without departing from the spirit of the present invention. For example, the present invention is applicable as a medical treatment device to be used in MRI with the use of a nonmagnetic metal, and as a medical treatment device to be used in X-rays with the use of a magnetic metal.

REFERENCE SIGNS LIST

1: medical treatment device
2: electrode portion
11: main body portion
12: connector
13: outer cylindrical tube (also referred to as shaft portion)
14: movable handle
14-2: fixed handle
15: turning member
16: conductive rod
17: electrode opening/closing (operation) rod
18: upper blade electrode (first electrode)
19: lower blade electrode (second electrode)
30: central electrode
31: shielding tube as insulator
32: grounded pipe as conductor
33: shielding holder
33(a) (b): shielding holder part
33(c): neck portion of shielding holder 33
34: bent holder
35: clasp
36: shielding cap
37: fixation cap
37(a): hole having notch
38: screw
39: turning shaft
40: mounting position
41: semicircular groove
42: semicircular flange
43(a), 43(b): semicircular groove
44(a), 44(b): semicircular groove
45: towing rod
46: towing wire
47: connection tube
48: guide tube
49: link pin
50: main body cover made of resin
50(a), 50(b): main body cover part
60a, 60b, 60c, 60d, 60e, 60f: screw
70: cylindrical mounting member
71: cylindrical member
72: partition wall
73: coil spring
74: turning fulcrum
75a, 75b: ring
76: sliding bar
77a, 77b: sliding pin
78: long hole
79: cylindrical member
80: switch
81: signal line

The invention claimed is:

1. A medical treatment device, comprising:
(i) an electrode portion having a grasping function, a coagulating function, and a cutting function, wherein said electrode portion further comprises:
a first electrode; and
a second electrode arranged opposed to said first electrode,
(ii) an operation portion for executing drive of said grasping function, said coagulating function, and said cutting function of said first electrode and said second electrode;
(iii) a shaft portion for connecting said electrode portion and said operation portion, wherein said shaft portion comprises:
on an outer side thereof, an outer cylindrical tube, and
on an inner side thereof, wherein said inner side comprises:
a conductive rod for supplying a microwave to said electrode portion, wherein said conductive rod comprises a coaxial cable, and
an electrode operation rod comprising a towing wire that uses a flexible tubular structure as a guide for transmitting the operation force from said operation portion to said electrode portion, wherein said shaft portion and said electrode portion are connected to each other with a bent holder that is provided continuously from said shaft portion, and includes said outer cylindrical tube, said conductive rod, and said electrode operation rod, and wherein said outer cylindrical tube, said conductive rod, and said electrode operation rod each has a curving angle substantially the same as a curving angle of said bent holder in the same direction;

(iv) a connector portion, which is provided at one end of said operation portion and is connectable to a microwave power source; and (v) a turning member located at a connection portion between said shaft portion and said operation portion, for rotating a shaft to rotate said bent holder, wherein said medical treatment device utilizing the microwave being configured to:

hold body tissue between said first electrode and said second electrode;

coagulate the body tissue by supplying the microwave to said electrodes; and cut the body tissue through a mutual action of said first electrode and said second electrode.

2. The medical treatment device according to claim 1, wherein said bent holder has a structure with divisions, in which divided parts are integrated.

3. The medical treatment device according to claim 1, wherein:

said conductive rod inside said bent holder is covered with a shielding holder; and said shielding holder has a structure with divisions, in which divided parts are integrated.

4. The medical treatment device according to claim 3, wherein said shielding holder for the conductive rod comprises a nonconductive member.

5. The medical treatment device according to claim 1, wherein:

said electrode operation rod, which is provided inside said bent holder, is provided inside a guide tube; and at least a curved portion of said guide tube has a flexible tubular structure.

6. The medical treatment device according to claim 5, wherein said flexible tubular structure comprises a flexible tubular member or a closed coil.

7. The medical treatment device according to claim 1, wherein said bent holder has a curving angle in a range of 1 degree to 90 degrees.

8. The medical treatment device according to claim 1, wherein said first electrode and said second electrode comprise a turnable operation blade and a fixed blade and comprise an opening and closing function or a sliding function so that said first electrode and said second electrode are configured to being shifted relative to each other.

9. The medical treatment device according to claim 1, wherein said first electrode and said second electrode are subjected to coating which prevents coagulated tissue from adhering.

10. The medical treatment device according to claim 1, wherein:

said first electrode turns in accordance with a front and rear movement of said electrode operation rod and said second electrode is fixed, said first electrode turning about a turning shaft; and said medical treatment device is configured to:

hold the body tissue between said first electrode and said second electrode by turning said first electrode;

coagulate the body tissue; and shear the body tissue by further turning said first electrode.

* * * * *